United States Patent [19]

Bemis et al.

[11] 4,430,073
[45] Feb. 7, 1984

[54] SURGICAL SUCTION PROBE WITH REVERSIBLE VALVE

[75] Inventors: Peter F. Bemis, Sheboygan; Gerald W. Swart, Sheboygan Falls, both of Wis.

[73] Assignee: Bemis Manufacturing Company, Sheboygan Falls, Wis.

[21] Appl. No.: 374,103

[22] Filed: May 3, 1982

[51] Int. Cl.³ .............................................. A61M 31/00
[52] U.S. Cl. ...................................... 604/48; 604/65; 604/249; 604/902
[58] Field of Search ................... 604/902, 48, 65, 246, 604/249, 19, 27, 22; 433/95; 251/347

[56] References Cited

U.S. PATENT DOCUMENTS

| | | | |
|---|---|---|---|
| 2,538,662 | 1/1951 | Abbott | 604/249 |
| 3,071,402 | 1/1963 | Lasto et al. | 604/249 |
| 3,146,987 | 9/1964 | Krayl | 251/100 |
| 3,232,578 | 2/1966 | Cousins | 251/302 |
| 3,321,178 | 5/1967 | Pinke et al. | 251/347 |
| 3,335,727 | 8/1967 | Spoto | 128/276 |
| 3,645,497 | 2/1972 | Nyboer | 251/148 |
| 3,707,972 | 1/1973 | Villari et al. | 128/274 |
| 3,794,290 | 2/1974 | Huszar | 251/347 |
| 3,958,573 | 5/1976 | Wiley | 128/276 |
| 4,015,336 | 4/1977 | Johnson | 604/249 |
| 4,081,176 | 3/1978 | Johnson | 251/342 |

FOREIGN PATENT DOCUMENTS 336529  5/1921  Fed. Rep. of Germany ...... 251/347

*Primary Examiner*—C. Fred Rosenbaum
*Assistant Examiner*—J. L. Kruter
*Attorney, Agent, or Firm*—Dressler, Goldsmith, Shore, Sutker & Milnamow, Ltd.

[57] ABSTRACT

An improved surgical suction probe includes a tubular probe portion and a tubular handle portion joined together to define an internal bore. A reciprocable one-piece valve is disposed within the bore and is movable between flow and non-flow positions for regulating flow of material through the probe. The components of the probe may be easily and inexpensively fabricated from plastic or other suitable material, thus providing a suitable suction probe arrangement with the necessary operational characteristics which may be fabricated inexpensively for single use service.

11 Claims, 6 Drawing Figures

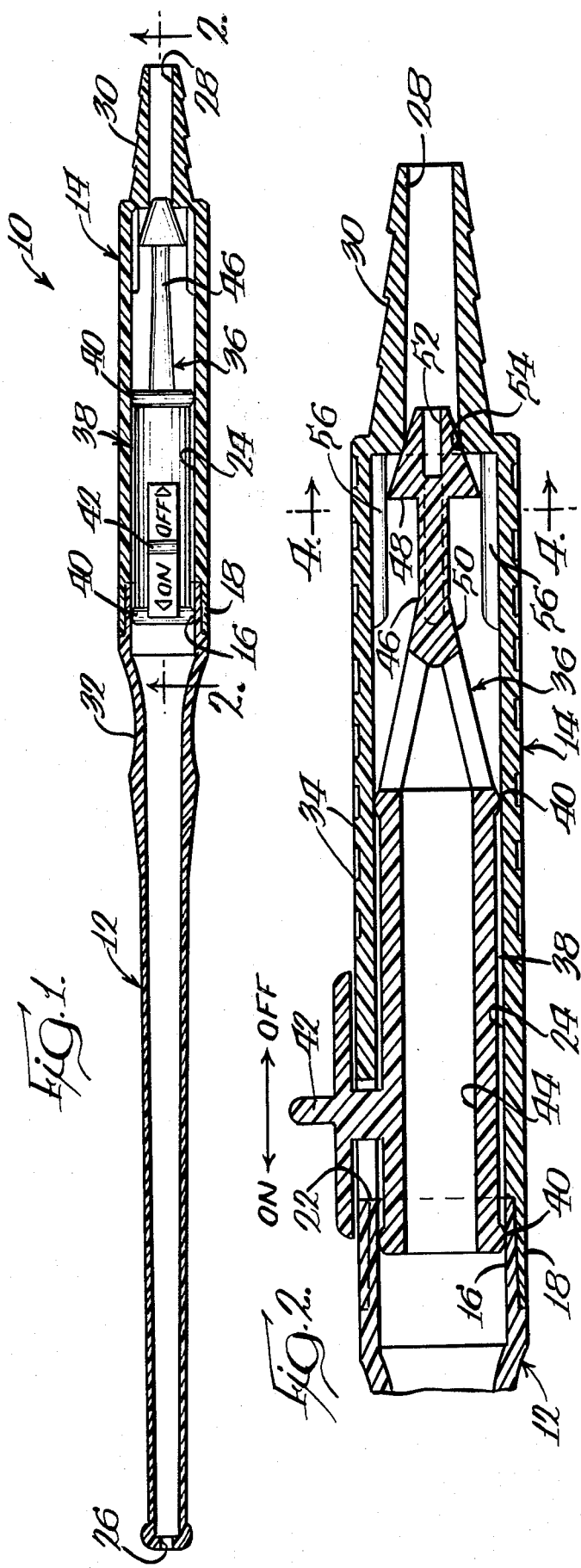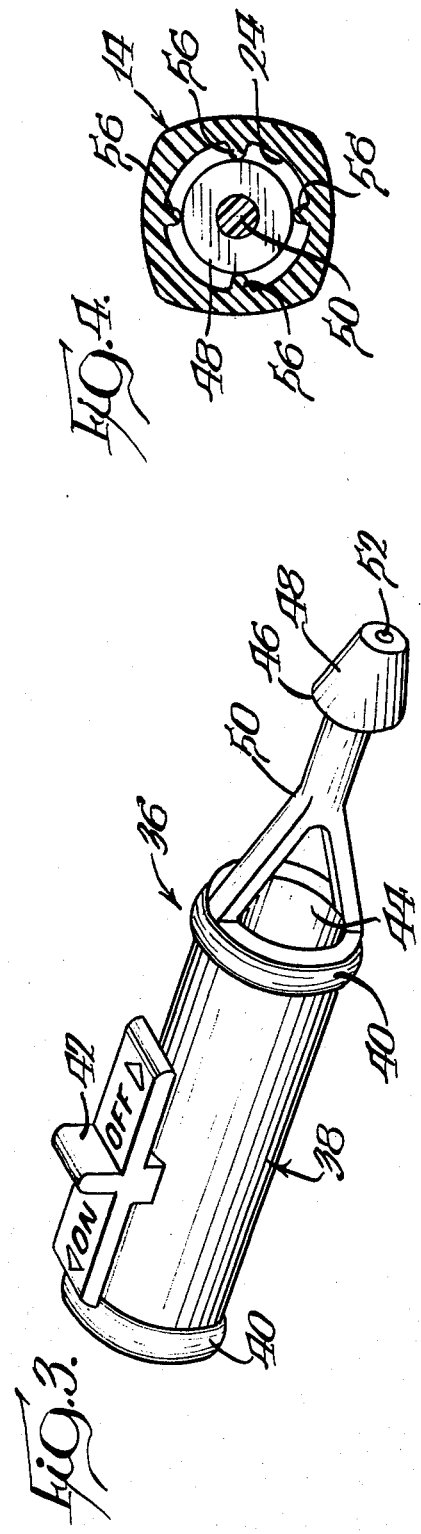

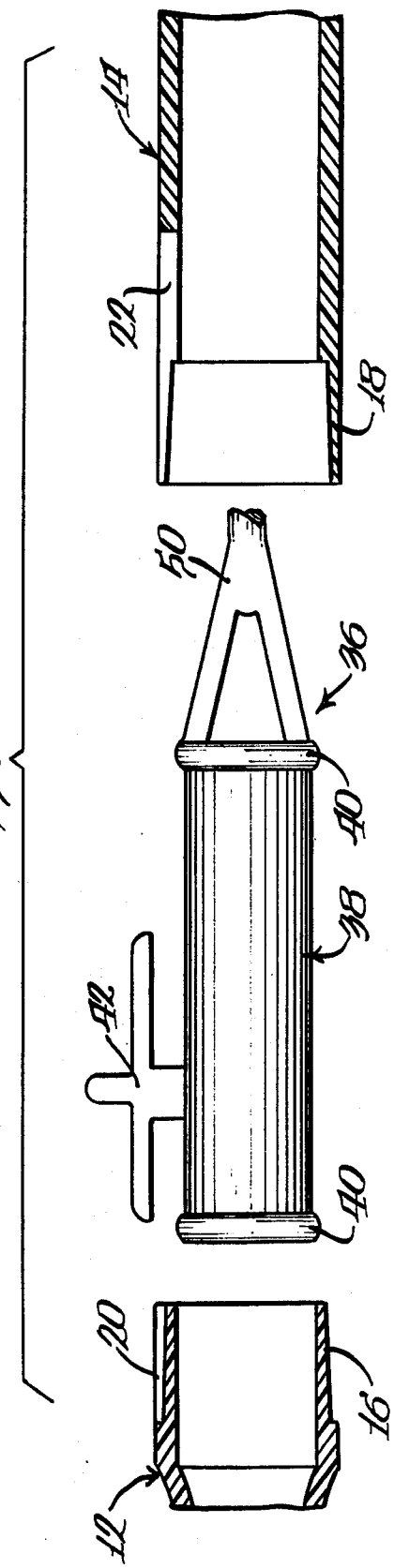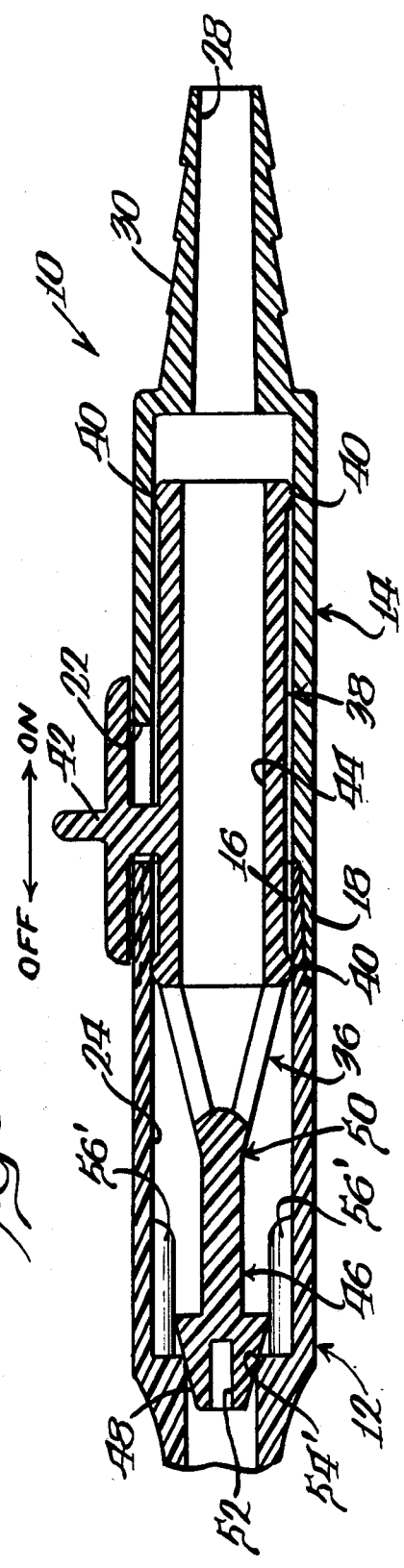

SURGICAL SUCTION PROBE WITH REVERSIBLE VALVE

FIELD OF INVENTION

This invention pertains generally to surgical instruments, and more particularly to a valved, surgical suction probe which may be inexpensively fabricated so that the probe is suited for single-use service.

BACKGROUND OF THE INVENTION

Suction probes and similar suction devices are uniformly used during all manner of surgical operations. A probe of this description typically includes an elongated probe portion which is adapted to be connected to a source of suction. The probe may be manipulated by surgical personnel during operations to remove blood, separated tissue, and other material from the patient.

The simplest suction probes heretofore known include a hollow tube which is joined to a source of suction at one end using a flexible hose or conduit. The free end of the tube can then be positioned in order to apply suction to the desired area. A vent aperture may be provided on the exterior of the probe tube so that suction is provided at the end of the tube whenever a user's fingers close the vent aperture. When the vent aperture is opened, the suction effect at the free end of the probe is discontinued.

There are several disadvantages to this simple design. Because the vacuum supply must be turned on throughout the operation in which the probe is used, there is the constant sound of air and/or liquid rushing through the probe. This acts to increase the noise level of the operating room, and may distract surgical personnel and require them to speak in raised voices to be heard. Additionally, since the source of vacuum is continually applied to the probe tube, there is a constant drain on the hospital's central vacuum system, thus diminishing vacuum levels throughout the hospital. Further, the freedom of the user's fingers is restricted since one finger must be placed over the vent aperture in order to provide suction at the end of the probe. If the finger were to slip from the vent aperture, the suction effect is immediately lost, which is highly undesirable.

Thus, the use of a suction probe which includes a valve arrangement for selectively turning on and off the suction effect is desirable, and overcomes some of the disadvantages normally associated with use of a simple suction probe as described above. Preferably, a valved suction probe is simple and inexpensive to manufacture so as to be disposable after a single use. Additionally, a valved suction probe is preferably capable of being readily cleaned and autoclaved for sterilization. Further, it must be lightweight, reliable, safe, and easily operable.

SUMMARY OF THE INVENTION

The surgical suction probe of the present invention is a simple, inexpensive, easily manufactured arrangement which is suitable and intended for disposal after a single use. The probe includes a valving arrangement which may be easily manipulated by surgical personnel between on and off positions so that suction is created at the end of the probe only when desired. Thus, demands put upon the suction system are minimized, and any hissing noises from the source of suction are eliminated when the probe is not in use.

The present suction probe comprises a tubular probe portion and a tubular handle portion joined together to define an internal bore. Suction is selectively provided at an opening at one end of the probe portion when the handle portion is joined to the source of suction.

Selective actuation of the probe is provided by a reciprocable one-piece valve element disposed within the internal bore. The one-piece valve includes a tubular body portion which includes annular sealing lands at either end thereof which engage and seal against the probe and handle portions defining the internal bore of the probe. An integral switch extends from the tubular body portion of the valve to the exterior of the probe for manipulating the valve between flow ("on") and non-flow ("off") positions. Material flowing through the probe flows into the opening at the probe portion, passes through the interior of the tubular body portion of the valve as it flows through the internal bore of the probe, and is drawn out of the probe through the end of the handle portion connected to the source of suction.

The reciprocable one-piece valve further includes an integral stopper plug portion. The stopper plug portion is spaced axially from the body portion of the valve, and is adapted to engage and seal against a valve seat defined by one of the probe portion and handle portion of the suction probe assembly. Movement of the valve within the internal bore of the probe by manipulation of the switch moves the stopper plug of the valve with respect to the valve seat, in this way regulating suction applied to the end opening of the probe assembly.

One of the significant features of the subject suction probe assembly is the versatility of operational characteristics provided by modifications of the design. This is achieved by alternative dispositions of the stopper plug of the valve within the internal bore, and by varying the tightness of the fit of the sealing lands provided on the body portion of the valve within the internal bore of the assembly. For instance, if the sealing lands on the valve body which are provided to engage the probe and handle portions of the assembly are provided with a relatively loose fit, the probe assembly may be made self-actuating. Thus, if the stopper plug of the valve engages a valve seat defined by the handle portion of the probe, the source of suction acts to draw the stopper plug into engagement with the valve seat to block flow through the probe, in which case the probe assembly is "self-closing." Conversely, if the valve seat is defined by the probe portion of the assembly, suction applied to the probe would draw the stopper plug of the valve out of engagement with the valve seat, whereby the probe would be "self-opening." Either of these arrangements are desirable since they preclude the necessity of the probe's user continually manipulating the probe to obtain the desired operation.

In other embodiments, the sealing lands provided on the body portion of the valve snugly frictionally engage the handle and probe portions of the assembly which define the internal bore. In this way, the amount of suction applied to the opening at the end of the probe may be easily regulated by the probe's user, with the valve of the probe assembly then maintaining the position selected by the user. This facilitates selection of the desired amount of suction without constant manipulation of the probe valve by the user.

Thus, the surgical suction probe of the present invention provides a highly versatile arrangement which may be inexpensively manufactured, yet provides desired operational characteristics for safe and efficient use.

Numerous other advantages and features of the present invention will become readily apparent from the following detailed description of the invention and embodiments thereof, from the claims and from the accompanying drawings in which like numerals are employed to designate like parts throughout the same.

BRIEF DESCRIPTION OF THE DRAWINGS

FIG. 1 is a plan view in partial cross-section of the surgical suction probe of the present invention;

FIG. 2 is an enlarged cross-sectional view taken along lines 2—2 of FIG. 1;

FIG. 3 is perspective view of the one-piece valve of the surgical suction probe shown in FIG. 1;

FIG. 4 is a cross-sectional view taken along lines 4—4 of FIG. 2;

FIG. 5 is a partial, exploded assembly view of the suction probe illustrated in FIG. 1; and FIG. 6 is a view similar to FIG. 2 illustrating a further embodiment of the surgical suction probe of the present invention.

DETAILED DESCRIPTION

While the present invention is susceptible of embodiment in different forms, there is shown in the drawings and will hereinafter be described various embodiments with the understanding that the present disclosure is to be considered as an exemplification of the invention and is not intended to limit the invention to the specific embodiments illustrated.

With reference to FIG. 1, therein is shown the surgical suction probe 10 of the present invention. The suction probe 10 is of a generally elongated configuration for facilitating manipulation by surgical personnel during an operation or other procedure where it is desired to provide selective application of suction to the patient. The probe 10 includes a tubular probe portion 12 and a tubular handle portion 14. As shown in FIGS. 2 and 5, probe portion 12 includes a probe flange 16, while handle portion 14 includes a handle flange 18. The flanges 16 and 18 may be tapered in a complementary fashion so that the probe portion 12 and handle portion 14 may be easily and securely joined together.

It will be observed that probe flange 16 includes a flange rib 20, while handle flange 18 is discontinuous. In this way, a switch slot 22 is defined by handle portion 14 and probe portion 12 after portions 12 and 14 have been fitted together.

When joined, probe portion 12 and handle portion 14 define generally cylindrical internal bore 24. Probe portion 12 defines a probe inlet opening 26 at the free or distal end thereof, through which material to be drawn from the patient enters the probe assembly. A suction opening 28 is defined by handle portion 14 which includes a suction fitting 30 for connecting the probe 10 with a suitable source of suction by a flexible conduit or hose. The fitting 30 may have a step-like profile for facilitating secure fitting with a flexible hose or the like and to accomodate attachment to hoses of varying diameters.

Easy use and manipulation of the probe 10 is facilitated by the inclusion of finger grip 32 on the probe portion 12. Similarly, ridges 34 may be provided on handle portion 14 whereby the user of the probe is able to maintain a secure grip on it when desired even if the probe or the user's fingers are slippery.

Because the probe 10 is primarily intended for single use service, each of probe portion 12 and handle portion 14 may be easily and inexpensively fabricated from plastic or other suitable material by an injection or compression molding process. The simple and straightforward design of these elements facilitates ready fabrication in this manner. Additionally, one or both of portions 12 and 14 may be made of transparent material so that flow of material through probe 10 may be readily observed.

In order to effectively regulate the suction effect provided by the probe 10 at the inlet opening 26, the probe further includes a reciprocable one-piece valve 36 disposed within the internal bore 24. It is contemplated that one piece valve 36 be simply and inexpensively fabricated of plastic or other suitable material so that the probe 10 is suitable for inexpensive, single-use service.

As shown in FIGS. 2-5, valve 36 includes a generally cylindrical, tubular valve body portion 38. The body portion 38 includes a pair of spaced annular sealing lands 40 which extend integrally about the exterior of the body portion 38 at either end thereof. The sealing lands 40 extend about the periphery of the body portion 38, and act as "0 rings" for sealing the valve 36 against the interior of handle and probe portions 14 and 12.

The valve 36 further includes a switch 42 integral with body portion 38 intermediate sealing lands 40. Valve 36 is positioned within the internal bore 24 such that the switch 42 extends through and is movable within switch slot 22. Manipulation of switch 42 by surgical personnel reciprocates valve 36, thus moving it between a non-flow "off," position and a flow, "on," position for regulating the suction and flow of material through probe 10.

As best shown in FIG. 2, the body portion 38 of valve 36 includes an interior bore 44. Flow of material through the probe 10 is provided through tubular probe portion 12, through the internal bore 24 via interior bore 44 of body portion 38 of the valve 36, and out of suction opening 28. Because sealing lands 40 are respectively disposed on opposite sides of switch 42, switch slot 22 is isolated from the flow of material through the probe 10. As will be discussed, depending upon the operational characteristics desired, sealing lands 40 may engage and seal against the interior of probe portion 12 and handle portion 14 so that valve 36 is freely reciprocable within internal bore 24, or may snugly engage the interior of portions 12 and 14 so that valve 36 is maintained in any position set by the user of the probe by manipulation of the switch 42.

In order to regulate flow of material through the probe 10, valve 36 includes an integral stopper portion 46. Stopper portion 46 includes a frustoconical stopper plug 48 which is maintained in fixed, spaced relation to tubular body portion 38 by a bifurcated stopper support 50. The stopper support 50 is integral with body portion 38 such that material moving through the probe flows through interior bore 44 of body portion 38 and about stopper support 50. Stopper plug 48 may include a plug hole 52 extending therein, hole 52 providing additional resiliency for the plug 48 in order to effect proper seating and sealing by the plug.

As best shown in FIG. 2, handle portion 14 of probe 10 defines a valve seat 54 against which stopper plug 48 of valve 36 seats for blocking suction and flow of material through the probe 10 when the valve 36 is in the non-flow position. When switch 42 is manipulated to move valve 36 to the flow position, stopper plug 40 is withdrawn from engagement with valve seat 54, and suction opening 28 is in communication with internal bore 24 so that suction and flow through probe 10 is provided. Notably, valve 36 may be positioned between the fully closed non-flow position and the fully opened flow position so that stopper plug 48 throttles or regulates suction and flow through the probe. As shown in FIGS. 2 and 4, a plurality of valve guides 56 integral with handle portion 14 extend axially of the internal bore 24, and are adapted to engage stopper plug 48 for guiding the movement of valve 36.

Operation of suction probe 10 is provided as follows. In this embodiment, sealing lands 40 provided on body portion 38 of valve 36 may be dimensioned such that they seal against the interior of probe portion 12 and handle portion 14 relatively loosely without binding, so the valve 36 is freely reciprocable within internal bore 24. When the probe 10 is connected with a source of suction by suction fitting 30, the suction pulls on stopper plug 48 and draws it into engagement with valve seat 54 so that valve 36 of automatically positioned in its non-flow position with plug 48 firmly engaging valve seat 54. In this position, suction opening 28 is blocked so that there is no flow through the probe 10 while it remains ready for use. Thus, in this embodiment probe 10 may be "self-closing." Notably, the closing of the suction in this manner prevents unnecessary demands on the central suction system of the hospital, and no discernible noise is made by the probe when not in use.

When it is desired to create suction for drawing fluid or other material through opening 26 at the end of probe portion 12, switch 42 may be easily manipulated by surgical personnel for repositioning valve 36 within the internal bore 24. Thus, if valve 36 is moved to the left, as viewed in FIG. 2, stopper plug 48 is disengaged from valve seat 54 thereby creating suction within the probe assembly. Valve 36 is in its fully open flow position when stopper plug 48 has been fully withdrawn from valve seat 54. As noted, movement of the valve 36 between the extreme flow and non-flow positions acts to regulate or throttle flow through the probe assembly. Sealing lands 40 isolate switch slot 22 from the flow of material within the probe, thus assuring clean, efficient, and readily adjustable operation of the surgical probe 10.

This embodiment of the present invention may be modified in order to provide different operational characteristics. Rather than providing a relatively loose fit of sealing lands 40 of the valve body 38 with the internal bore 24, sealing lands 40 may be dimensioned such that they engage and fit snugly against the interior of probe portion 12 and handle portion 14. By providing sufficient frictional engagement of the lands 40 with the interior of probe portion 14 and handle portion 12, valve 36 is maintained in a position in which it is placed by manipulation of the switch 42 by surgical personnel. Thus, rather than acting to automatically close suction opening 28 whenever pressure is released from the switch 42, the valve 36 may be automatically maintained in the flow position wherein stopper plug 48 is withdrawn from valve seat 54, the non-flow position when the plug 48 engages the valve seat 54, or at any selected position therebetween without continued manipulation of the switch 42 by surgical personnel. In this way, probe 10 may be easily positioned by its user for application of suction to the desired area without regard to specific placement of the user's fingers on the switch 42 or other portions of the probe 10. This modification to the probe 10 further enhances the versatility of its design.

With reference now to FIG. 6, a further embodiment of the surgical suction probe 10 is illustrated. As shown, probe 10 is similar to the probe illustrated in FIGS. 1 and 2, and comprises a similar probe portion 12 and handle portion 14 joined together by flanges 16 and 18 to define an internal bore 24 and a switch slot 22. A one-piece valve 36 is reciprocably disposed within the internal bore and is movable therein in response to manipulation of switch 42. It will be observed that in this embodiment of the suction probe 10, stopper plug 48 of the valve 36 is adapted to engage and seat against the valve seat 54' defined by probe portion 12 of the assembly. Probe portion 12 includes circumferentially spaced integral valve guies 56' (similar to valve guides 56 shown in FIG. 4) which are adapted to engage and guide stopper plug 48 of valve 36 as valve 36 reciprocates within internal bore 24. Flow through the probe 10 is blocked when stopper plug 48 engages and seats against valve seat 54'. When plug 48 is fully withdrawn from the valve seat 54', the valve 36 is in its flow position. Valve 36 may be positioned between the extreme flow and non-flow positions for regulation or throttling of flow of material and suction through the probe 10.

As previously described, sealing lands 40 may be provided to engage against the interior of probe portion 12 and handle portion 14 in one of two ways. If sealing lands 40 engage the interior of the probe such that the valve 36 is freely reciprocable therein, it will be appreciated that suction through suction opening 28 will act to automatically move valve 36 to its flow position and thus open the probe. The user of the probe may easily manipulate switch 42 in order to shut off or regulate flow through the probe, or may release switch 42 so that valve 36 is automatically moved to its flow position without continued manipulation of switch 42. Thus, this embodiment of probe 10 may be made to operate in a "self-opening" fashion.

In a modification of this further embodiment, sealing lands 40 may be provided such that they snugly fit against the interior of flow portion 12 and handle portion 14 with sufficient friction so that valve 36 maintains the position in which it is set by the probe's user by manipulation of switch 42. Thus, the probe's user may easily manipulate the switch 42 so that valve 36 regulates the flow through the probe in order to provide the amount of suction desired. The user can then remove their fingers from the switch 42 with the valve 36 in the desired position.

Thus, the present invention provides a simple, inexpensive, easily operable surgical suction probe which largely overcomes the disadvantages of arrangements heretofore known, and which may be made to provide various operational characteristics are provided as desired.

From the foregoing, it will be observed that numerous variations and modifications may be effected without departing from the true spirit and scope of the novel concept of the present invention. It will be understood that no limitation with respect to the specific embodiments illustrated and described herein is intended or should be inferred. It is, of course, intended to cover by the appended claims all such modifications as fall within the scope of the claims.

What is claimed is:

1. An improved surgical suction probe comprising:

a tubular probe portion having an opening at one end for drawing flowable material therein, a tubular handle portion, one end of which is joined to the other end of said probe portion and having an opposite end adapted to be operatively connected to an associated source of suction, said probe portion and said handle portion defining an internal bore when joined together, one-piece valve means reciprocably disposed within said internal bore and movable between a flow position wherein flowable material is drawn in said opening and through said internal bore of said probe by said suction, and a non-flow position wherein suction is blocked, flow through said probe being throttled when said valve means is between said flow and non-flow positions, said valve means including a tubular body portion through which said flowable material flows as said material flows through said internal bore, a switch integral with said body portion and extending through a slot defined by said probe and handle portions for manipulation by a user to position said valve means within said internal bore, a pair of sealing lands integral with said body portion, respectively disposed on opposite sides of said switch portion and engaging the interior of said probe portion and handle portion and isolating said slot from the interior of said tubular body portion, and a stopper portion integral with said body portion including a frustoconical stopper plug spaced from said body portion adapted to sealingly engage a valve seat defined by one of said probe and handle portions when said valve means is in said non-flow position.

2. The improved surgical suction probe of claim 1, wherein said valve seat is defined by said handle portion.

3. The improved surgical suction probe of claim 1, wherein said valve seat is defined by said probe portion.

4. The improved surgical suction probe of claims 1 or 3, wherein said valve means is automatically maintained in one of said flow and non-flow positions by said suction.

5. The improved surgical suction probe of claim 2 or 3, wherein said sealing lands frictionally engage the interior of said probe and handle portions which define said internal bore and to maintain said valve means in any position within said internal bore after manipulation of said switch.

6. A surgical suction probe comprising:

a tubular probe portion having an opening at one end for drawing flowable material therein, a tubular handle portion, one end of which is adapted to be joined to the other end of said probe portion and having an opposite end adapted to be operatively connected to an associated source of suction, said probe portion and said handle portion defining an internal bore when joined together, and valve means reciprocably disposed within said internal bore and movable between a flow position wherein flowable material is drawn in said opening and through said internal bore of said probe by said suction, and a non-flow position wherein said suction is blocked, flow through said probe being throttled when said valve means is between said flow and non-flow positions, said valve means including a tubular body portion through which said flowable material flows as said material flows through said internal bore, said body portion including sealing means engaging the interior of said probe and handle portions defining said internal bore, said valve means further including stopper means integral with said body portion adapted to engage a valve seat defined by one of said probe portion and said handle portion when said valve means is in said non-flow position, and switch means integral with said body portion and extending outwardly of said internal bore for manipulation by a user for moving said valve means between said flow and non-flow positions, wherein said valve means is automatically maintained in one of said flow and non-flow positions in response to said suction, and said handle portion defines said valve seat and said valve means is maintained in said non-flow position in response to said suction, and wherein said probe portion and said handle portion define a slot through which said switch means extend, and said sealing means comprise a pair of sealing lands respectively disposed on opposite sides of said switch means whereby said slot is isolated from fluid flow through said tubular body portion of said valve means.

7. A surgical suction probe comprising:

a tubular probe portion having an opening at one end for drawing flowable material therein, a tubular handle portion, one end of which is adapted to be joined to the other end of said probe portion and having an opposite end adapted to be operatively connected to an associated source of suction, said probe portion and said handle portion defining an internal bore when joined together, and valve means reciprocably disposed within said internal bore and movable between a flow position wherein flowable material is drawn in said opening and through said internal bore of said probe by said suction, and a non-flow position wherein said suction is blocked, flow through said probe being throttled when said valve means is between said flow and non-flow positions, said valve means including a tubular body portion through which said flowable material flows as said material flows through said internal bore, said body portion including sealing means engaging the interior of said probe and handle portions defining said internal bore, said valve means further including stopper means integral with said body portion adapted to engage a valve seat defined by one of said probe portion and said handle portion when said valve means is in said non-flow position, and switch means integral with said body portion and extending outwardly of said internal bore for manipulation by a user for moving said valve means between said flow and non-flow positions, wherein said sealing means frictionally engage the interior of said probe and handle portions whereby said valve means is maintained in position after manipulation of said switch means by the user, and wherein said handle portion defines said valve seat, and said probe portion and said handle portion define a slot through which said switch means extend, and said sealing means comprise a pair of sealing lands respectively disposed on opposite sides of said switch means whereby said slot is isolated from fluid flow through said tubular body portion of said valve means.

8. A surgical suction probe comprising:

a tubular probe portion having an opening at one end for drawing flowable material therein, a tubular handle portion, one end of which is adapted to be joined to the other end of said probe portion and having an opposite end adapted to be operatively connected to an associated source of suction, said probe portion and said handle portion defining an internal bore when joined together, and valve means reciprocably disposed within said internal bore and movable between a flow position wherein flowable material is drawn in said opening and through said internal bore of said probe by said suction, and a non-flow position wherein said suction is blocked, flow through said probe being throttled when said valve means is between said flow and non-flow positions, said valve means including a tubular body portion through which said flowable material flows as said material flows through said internal bore, said body portion including sealing means engaging the interior of said probe and handle portions defining said internal bore, said valve means further including stopper means integral with said body portion adapted to engage a valve seat defined by one of said probe portion and said handle portion when said valve means is in said non-flow position, and switch means integral with said body portion and extending outwardly of said internal bore for manipulation by user for moving said valve means between said flow and non-flow positions, wherein said valve means is automatically maintained in one of said flow and non-flow positions in response to said suction, and said probe portion defines said valve seat and said valve means is maintained in said flow position in response to said suction, and wherein said probe portion and said handle portion define a slot through which said switch means extend, and said sealing means comprise a pair of sealing lands respectively disposed on opposite sides of said switch means whereby said slot is isolated from fluid flow through said tubular body portion of said valve means.

9. A surgical suction probe comprising:

a tubular probe portion having an opening at one end for drawing flowable material therein, A tubular handle portion, one end of which is adapted to be joined to the other end of said probe portion and having an opposite end adapted to be operatively connected to an associated source of suction, said probe portion and said handle portion defining an internal bore when joined together, and valve means reciprocably disposed with said internal bore and movable between a flow position wherein flowable material is drawn in said opening and through said internal bore of said probe by said suction, and a non-flow position wherein said suction is blocked, flow through said probe being throttled when said valve means is between said flow and non-flow positions, said valve means including a tubular body portion through which said flowable material flows as said material flows through said internal bore, said body portion including sealing means engaging the interior of said probe and handle portions defining said internal bore, said valve means further including stopper means integral with said body portion adapted to engage a valve seat defined by one of said probe portion and said handle portion when said valve means is in said non-flow position, and switch means integral with said body portion and extending outwardly of said internal bore for manipulation by a user for moving said valve means between said flow and non-flow positions, wherein said sealing means frictionally engage the interior of said probe and handle portions whereby said valve means is maintained in position after manipulation of said switch means by the user, and said probe portion defines said valve seat, and wherein said probe portion and said handle portion define a slot through which said switch means extend, and said sealing means comprise a pair of sealing lands respectively disposed on opposite sides of said switch means whereby said slot is isolated from fluid flow through said tubular body portion of said valve means.

10. The improved surgical suction probe of claim 8 or 9, wherein said stopper means comprise a stopper plug spaced from said body portion of said valve means and support means extending between said body portion and said stopper plug whereby said stopper plug is maintained in fixed relation to said body portion and the interior of said body portion is in flow communication with said internal bore.

11. The improved surgical suction probe of claim 10, wherein the one of said probe portion and handle portion which defines said valve seat includes a plurality of integral valve guides spaced about said internal bore, said stopper plug being disposed in sliding relation to said guides as during reciprocable movement of said valve means within said bore.

* * * * *